United States Patent [19]

Kopf

[11] Patent Number: 4,666,703
[45] Date of Patent: May 19, 1987

[54] STORAGE-STABLE, QUICK-DISINTEGRATING PRESSED SHAPES CONTAINING PHARMACEUTICAL ACTIVE SUBSTANCES

[75] Inventor: Helmut Kopf, Rheinfelden, Switzerland

[73] Assignee: Ciba-Geigy Corporation, Ardsley, N.Y.

[21] Appl. No.: 711,137

[22] Filed: Mar. 13, 1985

[30] Foreign Application Priority Data

Mar. 23, 1984 [CH] Switzerland ............... 1465/84

[51] Int. Cl.$^4$ .................... A61K 9/28; A61K 9/32
[52] U.S. Cl. .................... 424/470; 424/80; 424/81; 424/465; 514/960; 514/781
[58] Field of Search .................... 424/19–22, 424/32, 35

[56] References Cited

FOREIGN PATENT DOCUMENTS

| 008780 | 3/1980 | European Pat. Off. . |
| 1380171 | 1/1975 | United Kingdom . |
| 1393374 | 5/1975 | United Kingdom . |
| 1540754 | 2/1979 | United Kingdom . |
| 2087235 | 5/1982 | United Kingdom . |
| 2086725 | 5/1982 | United Kingdom . |

OTHER PUBLICATIONS

CA 82:64453a Use of Aqueous Dispersions of Synthetic Materials to Coat Drug Forms, (1975).
Unlisted Drugs 31, No. 9 (Sep. 1979), p. 133.
Unlisted Drugs 31 No. 4 (Apr. 1979), p. 52.
Kornblum, et al. (11), J. Pharma Sei 62(1), 43–48, Jan. 1973, New Tablet Disintegrating Agent: Cross Linked Polyvinylpyrrolidine.
Stozek et al., CA 87: 189398w (1977).
Krowcyznski et al., CA 89: 80174k (1978).
Lippold et al., CA 94: 52812b (1981).
Trade Literature "Eudragit E30D" pp. 1–7, Eudragits and Eudragit L.
Trade Literature "Aquacoat ECD-30", Section 1, Monograph.

Primary Examiner—Shep K. Rose
Attorney, Agent, or Firm—Michael W. Glynn; Irving M. Fishman

[57] ABSTRACT

Storage stable, quick-disintegrating pressed shapes containing pharmaceutical active substances, which shapes consist substantially of a compressed mixture of
(a) an effective amount of a pharmaceutical active substance in granular form, which is coated with a coating material comprising essentially a homogeneous mixture of a poly(H+meth)-acrylic acid-(methyl-+ethyl) ester insoluble but dispersible in water and an ethyl cellulose insoluble but dispersible in water, the weight ratio of the acrylic acid ester to ethyl cellulose being 2.5:1 to 5:1;
(b) talcum; and
(c) colloidal silicon dioxide, and crosslinked polyvinylpolypyrrolidone as the disintegrating agent having a high disintegrating capacity and good binding properties.

5 Claims, No Drawings

STORAGE-STABLE, QUICK-DISINTEGRATING PRESSED SHAPES CONTAINING PHARMACEUTICAL ACTIVE SUBSTANCES

The invention relates to storage-stable, quick-disintigrating pressed shapes containing the pharmaceutical active substance in a granular delayed-release form.

It is known that pharmaceutical active substances can be mixed together and coated with auxiliaires retarding the release of the active substances, the mixture then being processed into the form of granules, which can either be administered directly in this form, or be administed after being filled into capsules or after further processing into tablet form. Granular delayed-release forms of pharmaceutical active substances known hitherto have various disadvantages. There were difficulties for example in connection with their production. Either the mode of production was complicated because, for example, the use of organic solvents was necessary, or the auxiliaires used were not ideal with regard to the effect aimed at, namely, the correctly delayed release of active substances. Problems arose also with respect to the properties of these granules, for example unsatisfactory free flowability or sensitivity to moisture, disadvantages which became evident either with the direct administration, that is to say, with dosing and possibly with the simultaneous taking of food or stimulants, or with the filling of the capsules. Furthermore, individual doses of above 600 mg filled into capsules are not advantageous since the corresponding capsules are too large to be swallowed. There were therefore suggested quick-disintegrating pressed shapes containing the active substance, which consist essentially of a compressed mixture comprising (a) an active substance in a granular delayed-release form and (b) a disintegrating agent having a high disintegrating capacity as well as good binding properties.

For this purpose, the active substances in the granular delayed-release form were used as coated granules, the coating of which consists in the main of a homogeneous mixture of a polyacrylate insoluble but dispersible in water and a cellulose ether insoluble but dispersible in water (European Patent Application No. EP-A 0,052,076).

The two coating materials used are known as such; employed individually, however, they are not suitable for the purpose of the present invention. The first-mentioned coating material is very thermoplastic and coated granules produced therewith tend to stick together. The second-mentioned on the other hand, when used in customary amounts and in normal processing, gives a coating which has an insufficient retarding effect. The combination of the coating materials, individually unsuitable for the present purpose, gives however a very good result. The pharmaceutical active substance granules produced according to the present invention are hence free-flowing, insensitive to moisture and neutral in taste, and they result in the desired delayed release of active substance with great uniformity. It has moreover been established by microscopic examinations that the individual active-substance granule is very evenly coated, so that it substantially retains its original shape.

Active substances suitable for the known granular delayed-release form of pharmaceutical active substances are, inter alia, granular or crystalline substances. Especially suitable are solid granules or monocrystals within the range of size of 0.3–2 mm (diameter), which have a certain mechanical strength, a property which is of special importance in the subsequent processing of the granules into pressed shapes.

Suitable as coating materials are on the one hand polyacrylates of the formula

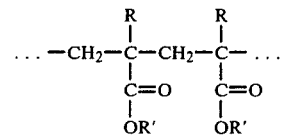

R = H, CH$_3$
R' = CH$_3$, C$_2$H$_5$.

Substances of this type are obtainable by emulsion polymerisation, and they contain the copolymer having a molecular weight of some 100,000 in the form of latex particles with a diameter of around or below 1 μm. A corresponding product which is particularly suitable is sold by Röhm Pharma GmbH, Darmstadt (Fed. Rep. of Germany) under the name of Eudragit ®E3OD; this is in the form of an aqueous dispersion, and is an ethyl acrylate/methyl methacrylate 70:30 copolymer having a molecular weight of 800,000.

And on the other hand the coating material used is ethyl cellulose. A particularly suitable product is that sold by FMC Corporation, Philadelphia, (Pa., USA) under the name of Aquacoat ®ECD-30, this being in the form of a 30% aqueous polymeric dispersion having a low particle size (latex form) and a narrow particle-size distribution.

The above two coating materials (poly(H+meth)-acrylic acid-(methyl+ethyl) ester and ethyl cellulose) are used in the weight ratio of 2.1:1 to 5:1, particularly however in the ratio of 3:1.

As suitable disintegrating agents having a high disintegrating capacity and good binding properties for the formed shapes obtainable according to the invention, there are used crosslinked polyvinylpolypyrrolidone (PVPP-XL), for example Polyplasdone ®XL, marketed by the GAF Corporation, New York, N.Y. (USA), or Kollidon ®CL (BASF, Ludwigshafen/Rhein, Fed. Rep. of Germany). In order to counteract separation phenomena between the relatively large coated pharmaceutical active-substance granules and the relatively small disintegrating-agent particles, a portion of the disintegrating agent can be replaced by microcrystalline cellulose (for example Avicel ®), the good disintegrating properties being fully retained. A mixture of PVPP-XL and Avicel in the ratio of 1:1.3 to 1.5 is preferred.

With regard to the auxiliaries otherwise customarily used for tabletting, these are in particular binders, lubricants and antisticking agents.

The quick-disintegrating pressed shapes containing the pharmaceutical active substance which are produced according to the prior art certainly have a disadvantage: they are not storage-stable at higher temperatures, that is to say, above 20° C., in consequence of which the disintegration time is considerably increased, so that the desired therapeutic effect can no longer be ensured.

It has now been found that, surprisingly, an excellent storage stability at elevated temperatures can be obtained when the finished coated granules are mixed not only with small amounts of colloidal silicon dioxide (for example the Aerosil ® marketed by Degussa, Frankfurt [Fed. Rep. of Germany]], but also with small amounts of talcum.

The storage-stable, quick-disintegrating pressed shapes containing the pharmaceutical active substance which are obtained according to the present invention hence consist substantially of a compressed mixture of (a) an effective amount of a pharmaceutical active substance in granular form, which is coated with a coating material comprising essentially a homogeneous mixture of a poly(H+meth)-acrylic acid-(methyl+ethyl) ester insoluble but dispersible in water and an ethyl cellulose insoluble but dispersible in water, the weight ratio of the acrylic acid ester to ethyl cellulose being 2.5:1 to 5:1;

(b) talcum; and (c) colloidal silicon dioxide, and crosslinked polyvinylpyrrolidone as the disintegrating agent having a high disintegrating capacity and good binding properties.

The pharmaceutical active-substance granules used according to the invention can be produced in a manner known per se. They are produced in the fluidised-bed spraying apparatus known for this purpose, or in coating pans. The coating-material mixture is fed in as an aqueous dispersion at about 30° C., and spraying is best performed with air at a temperature of 25° to 30° C. The individual coated granules are obtained in this manner, that is to say, no undesirable agglomeration of granules occurs. The pharmaceutical active-substance granules thus obtained are firstly mixed with talcum. The resulting active-substance granules can then readily be pressed together with colloidal silicon dioxide, crosslinked polyvinylpyrrolidone as the disintegrating agent having a high disintegrating capacity and good binding properties, and with the customary auxiliaries otherwise used for forming tablets, within a wide dosage range into moulded shapes, for example round or capsule-shaped compressed products. When a formed or moulded shape has to be produced with two or more active ingredients, the individually dyed pharmaceutical active-substance granules can be prepared separately, a factor which facilitates identification, and which renders the patient aware of the fact that the preparation being taken contains two or more active substances. Eventual second active substances can naturally be added also in the unretarded form.

The formed shapes thus obtained have the property of rapidly disintegrating into separate granules in the stomach of the person being treated and hence becoming well dispersed. A localised overconcentration of the active substance in the digestive tract is in this way prevented, and a uniform, slowly occurring release of active substance dispersed over a large resorption area is ensured. It has been verified by microscopic examination that the individual granules have not been damaged as a result of compression, so that on release of the active substance from the granules, the active substance is able to bring into effect its original advantageous properties virtually completely. The compressed shapes according to the invention are storage-stable also at elevated temperatures, that is to say, they possess disintegration properties which remain constant.

The usual tablet-compressing machines can be used for producing the formed shapes obtainable according to the invention.

Since the mechanical strength of the formed shapes is surprisingly good, it is possible to produce all the desired customary forms, for example round, capsule- or rod-shaped moulded products, with or without breaking grooves or imprints specific to the firm concerned.

All pharmaceutical active substances which can be used for peroral administration and for which a delayed release in the gastro-intestinal tract is desired are essentially suitable, in the form of granules or crystals of an appropriate size, for being processed according to the invention. The present invention is however particularly advantageous with respect to the use of active substances which, when used at a fairly high concentration, can cause local irritation of the mucous lining of the gastro-intestinal tract, and which are administered in large single doses. This applies for example in the case of potassium chloride administered in the treatment of calcium deficiency conditions, for example in the treatment with saliuretic diurectics, or in the case of lithium salts in psychotherapy. Where there is a formed shape with potassium chloride, it is possible for a second active substance, for example in the unretarded form, especially a diuretic (for example hydrochlorothiazide), to be incorporated into the auxiliaries. This can be effected for example by mixing the second active substance with the auxiliaries. When however there is a considerable difference between the particle size of the second active substance and that of the coated potassium chloride particles, a partial separation can occur, an effect which can lead to inaccurate dosing of the active substances. It can therefore be advantageous to firstly compress the second active substance, in the customary manner, to form a core, and subsequently to compress around this core the coated potassium chloride particles with the auxiliaries. On rapid disintegration of a formed shape of this type, the diuretic is immediately released and is also pharmacologically effective, whilst the potassium chloride, as mentioned, is released only gradually.

EXAMPLE 1

| Composition: | per dose | per batch |
|---|---|---|
| potassium chloride crystals having a particle size of 0.3–0.6 mm | 600.0 mg | 3000 g |
| Eudragit ® E30D solid | 140.0 mg | 700 g |
| Aquacoat ® ECD solid | 44.0 mg | 220 g |
| talcum (Pharmacopoe Helvetica) | 12.0 mg | 60 g |
| Aerosil ® 200 | 2.0 mg | 10 g |
| Avicel ® PH 101 | 68.0 mg | 340 g |
| Polyplasdone ® XL | 50.0 mg | 250 g |
| magnesium stearate | 4.0 mg | 20 g |
| | 920.0 mg | 4600 g |

Production (A) Coated granules

Potassium chloride is sprayed with a mixture of Endragit ®E3OD and Aquacoat ®ECD dispersions in a fluidised-bed granulator (for example fluidised-bed granulator Aeromatik AES 1.30), according to the co-current principle, with an inlet-air temperature of 28° C. and a throughput of about 80 g/minute. The mixture of the dispersions has to be stirred during the spraying operation. After the whole amount of the dispersion mixture has been sprayed on, the coated KCl is dried for about 10 minutes in the fluidised-bed dryer (for example fluidised-bed dryer Aeromatik AES 1.30) at 28° C. inlet-air temperature. The coated and dried KCl granules are then mixed with talcum for 10 minutes. The mixture is finally put through a 1.5–2.0 mm sieve in order to remove any possible KCl agglomerates.

(B) Pressed shapes

Avicel®PH 101, Polyplasdone®XL, Aerosil®200 and magnesium stearate are mixed with the mixture of coated KCl granules and talcum, produced according to A, for 10 minutes. The mixture thus prepared is compressed, on a commercial tablet-compressing machine (for example Kilian Pharma I), into the form of rod-shaped tablets 17.4×8.6 mm.

Disintegration properties of the tablets (disintegration tester USP, in water at 37° C.)

| After preparation | After 3 months' storage at 35° C. |
|---|---|
| <1 minute | <2 minutes |

Release properties of potassium chloride (modified USP disintegration tester, water 37° C.)
Percentage of active substance released

| After preparation | After 3 months' storage at 35° C. |
|---|---|
| after 1 hour 29% | 33% |
| after 2 hours 49% | 61% |
| after 3 hours 66% | 80%. |

EXAMPLE 2

| Composition | | |
|---|---|---|
| KCl granules coated and then treated with talcum, according to Example 1A | 796.0 mg | 796 g |
| hydrochlorothiazide granulate (see below) | 50.0 mg | 50 g |
| Avicel ® PH 101 | 68.0 mg | 68 g |
| Polyplasdone ® XL | 50.0 mg | 50 g |
| Aerosil ® 200 | 2.0 mg | 2 g |
| magnesium stearate | 4.0 mg | 4 g |
| | 970.0 mg | 970 g |

Production (A) 75 g of micronised hydrochlorothiazide, 1.5 g of Aerosil®200, 55.5 g of calcium hydrogen phosphate SP 2AQ and 18 g of sodium carboxymethyl starch are thoroughly mixed with 200 g of demineralised water; the mixture is then granulated in a fluidised-bed granulator STREA 1, and dried at 45° C. in a fluidised-bed dryer STREA 1. The dry granulate is subsequently reduced in size through a round sieve having a mesh size of 0.5 mm.

(B) 50 g of the comminuted granulate are thoroughly mixed with KCl granules coated and the treated with talcum, according to Example 1A. The above-mentioned tablet auxiliaries are subsequently mixed in, and the mixture is compressed, on a commercial tabletting machine (for example Korsch EKO), into the form of rodlets 16.4×8.6 mm.

Disintegration properties of the potassium chloride/hydrochlorothiazide tablets (USP disintegration tester, in water at 37° C.): <1 minute.

Release properties of potassium chloride after preparation of the tablets: as in Example 1.

EXAMPLE 3

| Composition: | per dose | per batch |
|---|---|---|
| coated KCl granules according to Example 1A | 796.0 mg | 796 g |
| hydrochlorothiazide granulate according to Example 2A | 50.0 mg | 50 g |
| Avicel ® PH 101 | 68.0 mg | 68 g |
| Polyplasdone ® XL | 50.0 mg | 50 g |
| Aerosil ® 200 | 2.0 mg | 2 g |
| magnesium stearate | 4.0 mg | 4 g |
| | 970.0 mg | 970 g |

Production (A) 50 g of the hydrochlorothiazide granulate, obtained according to Example 2A, are compressed, on a commercial tabletting machine for producing dry coated tablets (for example Manesty Dry Cota), into the form of round tablets having a diameter of 6 mm.

(B) Each of the tablets thus obtained is mechanically inserted into the ready for pressing mixture of the remaining constituents of the finished tablets, and the whole is compressed into rodlet-shaped tablets which are 14.4×8.6 mm in size (for example on the same machine as in A).

Disintegration properties of potassium chloride/hydrochlorothiazide coated tablets:

| hydrochlorothiazide tablet | <1 minute |
|---|---|
| whole tablet | <2 minutes |

Release properties of potassium chloride after preparation of the dry coated tablets: as in Example 1.

What is claimed is:

1. Storage-stable, quick-disintegrating pressed shapes containing pharmaceutical active substances, which shapes consist substantially of a compressed mixture of
   (a) an effective amount of a pharmaceutical active substance in granular form, which is coated with a coating material comprising essentially a homogeneous mixture of a poly(H+meth)-acrylic acid-(methyl+ethyl) ester insoluble but dispersible in water and an ethyl cellulose insoluble but dispersible in water, the weight ratio of the acrylic acid ester to ethyl cellulose being 2.5:1 to 5:1;
   (b) talcum; and
   (c) colloidal silicon dioxide, and crosslinked polyvinylpolypyrrolidone as the disintegrating agent having a high disintegrating capacity and good binding properties.

2. Pharmaceutical active-substance pressed shapes according to claim 1, wherein the mixture ratio of the coating materials is 3:1.

3. Pharmaceutical active-substance pressed shapes according to claim 1, wherein the disintegrating agent consists of a mixture of polyvinylpolypyrrolidone and microcrystalline cellulose.

4. Pharmaceutical active-substance pressed shapes according to claim 1, wherein the pharmaceutical active substance is potassium chloride having a particle size of 0.3–1.2 mm diameter.

5. Pharmaceutical active-substance pressed shapes according to claim 1, wherein the pharmaceutical active substance is potassium chloride having a particle size of 0.5–1.2 mm diameter.

* * * * *